US012532918B2

(12) United States Patent
Zuber et al.

(10) Patent No.: US 12,532,918 B2
(45) **Date of Patent: *Jan. 27, 2026**

(54) AEROSOL-GENERATING SYSTEM INCLUDING A HEATED GEL CONTAINER

(71) Applicant: Altria Client Services LLC, Richmond, VA (US)

(72) Inventors: Gerard Zuber, Neuchatel (CH); Jean-Yves Vollmer, Neuchatel (CH)

(73) Assignee: Altria Client Services LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/487,423

(22) Filed: Oct. 16, 2023

(65) Prior Publication Data

US 2024/0033448 A1 Feb. 1, 2024

Related U.S. Application Data

(63) Continuation of application No. 16/997,086, filed on Aug. 19, 2020, now Pat. No. 11,839,706, which is a (Continued)

(30) Foreign Application Priority Data

Jul. 29, 2016 (EP) .................................... 16181949

(51) Int. Cl.

*A24F 40/42* (2020.01)
*A24F 40/46* (2020.01)

(Continued)

(52) U.S. Cl.

CPC .............. *A24F 40/46* (2020.01); *A24F 40/42* (2020.01); *A61M 11/042* (2014.02);

(Continued)

(58) Field of Classification Search

CPC .......... A24F 40/42; A24F 40/30; A24F 40/20; A24F 40/40; A61M 15/06

See application file for complete search history.

(56) References Cited

U.S. PATENT DOCUMENTS

| | | | |
|---|---|---|---|
| 5,613,505 | A | 3/1997 | Campbell et al. |
| 2009/0320863 | A1 | 12/2009 | Fernando et al. |

(Continued)

FOREIGN PATENT DOCUMENTS

| | | |
|---|---|---|
| CN | 103960784 A | 8/2014 |
| CN | 104256888 A | 1/2015 |

(Continued)

OTHER PUBLICATIONS

Japanese Notice of Allowance for JP Application 2022-188549 dated Oct. 28, 2024 (2 pages).

(Continued)

*Primary Examiner* — Margaret M Luarca

(74) *Attorney, Agent, or Firm* — Harness, Dickey & Pierce, P.L.C.

(57) ABSTRACT

An aerosol-generating system may include an electrical power supply, an electrical heater connected to the electrical power supply, and a substrate container. The substrate container may define a blind cavity containing an aerosol-forming substrate in the form of a gel that is a solid at room temperature. The electrical heater is external to the substrate container and configured to heat the substrate container to generate a vapor without contacting the aerosol-forming substrate. As result, the possibility of unwanted materials building up on the electrical heater can be reduced, thereby providing a more reliable and consistent performance.

20 Claims, 7 Drawing Sheets

Related U.S. Application Data continuation of application No. 15/662,536, filed on Jul. 28, 2017, now Pat. No. 10,772,355, which is a continuation of application No. PCT/EP2017/066998, filed on Jul. 6, 2017.

(51) Int. Cl.

| | |
|---|---|
| ***A61M 11/04*** | (2006.01) |
| ***A61M 15/00*** | (2006.01) |
| ***A61M 15/06*** | (2006.01) |
| *A24F 40/20* | (2020.01) |
| *A61M 16/00* | (2006.01) |

(52) U.S. Cl.

CPC ........ *A61M 15/0036* (2014.02); *A61M 15/06* (2013.01); *A24F 40/20* (2020.01); *A61M 2016/0024* (2013.01); *A61M 2205/3368* (2013.01); *A61M 2205/8206* (2013.01)

(56) References Cited

U.S. PATENT DOCUMENTS

| | | | | |
|---|---|---|---|---|
| 2011/0200670 | A1 | 8/2011 | Thakkar | |
| 2013/0160765 | A1 | 6/2013 | Liu | |
| 2013/0330101 | A1 | 12/2013 | Gonzalez et al. | |
| 2014/0060554 | A1 | 3/2014 | Collett et al. | |
| 2014/0261472 | A1 | 9/2014 | Carroll et al. | |
| 2014/0366898 | A1 | 12/2014 | Monsees et al. | |
| 2016/0120224 | A1 | 5/2016 | Mishra et al. | |
| 2016/0120225 | A1 | 5/2016 | Mishra et al. | |
| 2017/0055574 | A1 | 3/2017 | Kaufman et al. | |
| 2017/0340005 | A1 * | 11/2017 | Terao | A24F 47/00 |
| 2018/0199628 | A1 | 7/2018 | Sheng | |

FOREIGN PATENT DOCUMENTS

| | | | | |
|---|---|---|---|---|
| CN | 104470382 | A | 3/2015 | |
| CN | 105029711 | A | 11/2015 | |
| CN | 105072935 | A | 11/2015 | |
| CN | 105473012 | A | 4/2016 | |
| EP | 0509657 | A1 | 10/1992 | |
| EP | 1886918 | B1 | 3/2009 | |
| EP | 2279677 | A1 | 2/2011 | |
| EP | 2550877 | A1 | 1/2013 | |
| EP | 2424392 | B1 | 4/2013 | |
| EP | 2488054 | B1 | 12/2013 | |
| EP | 3794999 | A1 | 3/2021 | |
| GB | 2524779 | A | 10/2015 | |
| JP | 2013-507906 | A | 3/2013 | |
| JP | 2015532828 | A | 11/2015 | |
| JP | 2017-503499 | A | 2/2017 | |
| RU | 107026 | U1 | 8/2011 | |
| RU | 157882 | U1 | 12/2015 | |
| RU | 2581999 | C2 | 4/2016 | |
| WO | WO-2013/126167 | A1 | 8/2013 | |
| WO | WO-2013128176 | A1 | 9/2013 | |
| WO | WO-2015101479 | A1 | 7/2015 | |
| WO | WO-2015/165814 | A1 | 11/2015 | |
| WO | WO-2015177043 | A1 * | 11/2015 | A24B 15/167 |
| WO | WO-2015/197627 | A1 | 12/2015 | |
| WO | WO-2016/005601 | A1 | 1/2016 | |
| WO | 2016/046362 | A1 | 3/2016 | |
| WO | WO-2016096927 | A1 | 6/2016 | |

OTHER PUBLICATIONS

Japanese Office Action for corresponding JP Application 2022-188549 dated Apr. 30, 2024, with English language translation (10 pages).

Japanese Office Action for JP Application 2022-188549 dated Oct. 30, 2023, with English language translation (17 pages).

European Search Report for European Application No. EP16181949 Dated Feb. 3, 2017.

Written Opinion for corresponding International Application No. PCT/EP2017/066998 dated Oct. 26, 2017.

International Search Report and Written Opinion for corresponding Application No. PCT/EP2017/066998 dated Oct. 30, 2017.

https://www.ecig-vapo.com/e-solid-ice-mint-p-105.html, retrieved on Dec. 12, 2018.

International Preliminary Report on Patentability for corresponding International Application No. PCT/EP2017/066998 dated Feb. 7, 2019.

Office Action for corresponding Russian Application No. 2019105591 dated Nov. 19, 2020.

Office Action for Chinese Application No. 201780042829.X dated Mar. 9, 2021 and English translation.

Notice of Refusal for Japanese Application 2019-502564 dated Apr. 5, 2021, and English translation (7 pages).

Office Action for corresponding Russian Application No. 2019105591 dated Jul. 2, 2021, with translation.

Office Action for Chinese Application 201780042829.X, dated Nov. 1, 2021, with translation.

Notice of Allowance in Israeli Application 263434 dated Sep. 19, 2021, English translation not available.

Decision on Grant for Russian Patent Application 2019105591 dated Oct. 4, 2021, with translation.

Office Action for corresponding Japanese Application No. 2019-502564, dated Dec. 15, 2021, with English language translation.

Office Action for Chinese Application No. 201780042829.X dated Mar. 2, 2022 and English translation.

European Communication Pursuant to Article 94(3) EPC for European Application No. 17737555.7 dated Mar. 2, 2022.

Japanese Office Action for JP Application 2019-502564 dated Jul. 25, 2022, with English language translation (5 pages).

South Korean Office Action for KR Application 2019-7002363 dated Aug. 5, 2022, with English translation (9 pages).

Japanese Pre-Appeal Review Report for JP Application 2019-502564 with English language translation (10 pages).

South Korean Office Action for KR Application 2019-7002363 dated Feb. 20, 2023 with English language translation (8 pages).

Office Action dated Mar. 11, 2024 issued in related Japanese patent application No. 2019-502564.

Japanese Office Action for JP Application 2019-502564 dated Oct. 10, 2023, with English language translation (37 pages).

Korean Notice of Allowance for KR Application 10-2019-7002363 dated Jan. 8, 2024, with English language translation (5 pages).

South Korean Office Action for KR Application 10-2019-7002363 dated Aug. 25, 2023, with English language translation (6 pages).

Canadian Office Action for corresponding CA Application 3,031,241, dated Sep. 11, 2023 (3 pages).

Japanese Office Action for JP Application No. 2019-502564 dated Aug. 26, 2022 (25 pages).

Japanese Office Action for JP Application 2024-206532 dated Jun. 23, 2025, with English translation.

Japanese Appeal Decision for JP Application 2019-502564 dated Jun. 17, 2025, with English translation.

Chinese Office Action for CN Application No. 201780042829.X dated Feb. 12, 2025.

"Controlled Release Technology and Its Application in Tobacco Flavors" by Wang Mingfeng et al., Southwest Jiaotong University Press, published on May 31, 2016, pp. 60-100 (English translation not available).

Chinese Board Decision for CN Application No. 201780042829.X dated Apr. 22, 2025.

Pharmaceutical Professional Knowledge 2, compiled by the National Medical Products Administration Licensed Pharmacist Certification Center, published by China Traditional Chinese Medicine Publishing House, with a publication date of Mar. 2003.

Polymer Blends and Alloys by Shen Jiarui et al., South China University of Technology Press, Sep. 1999, pp. 233-234.

* cited by examiner

FIG. 5
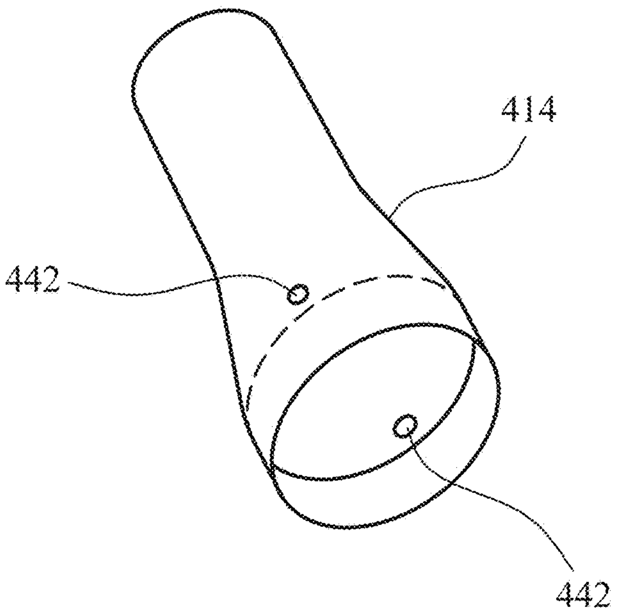
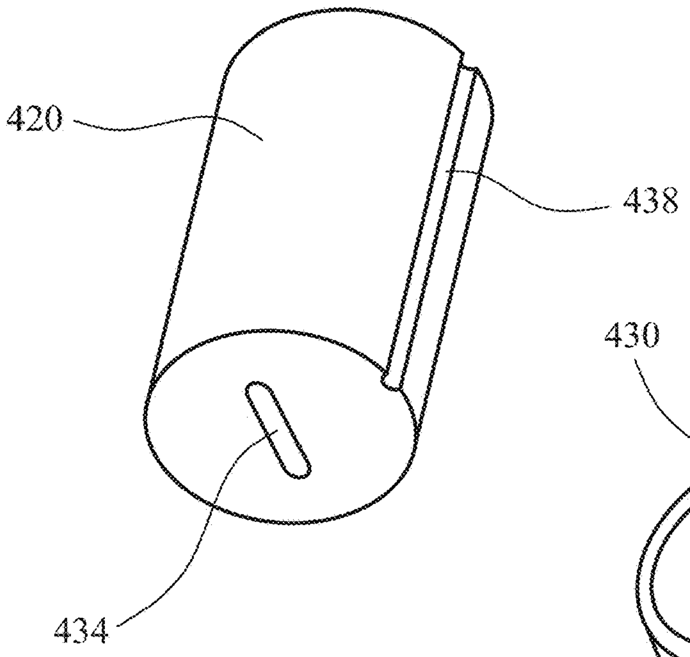
FIG. 6a
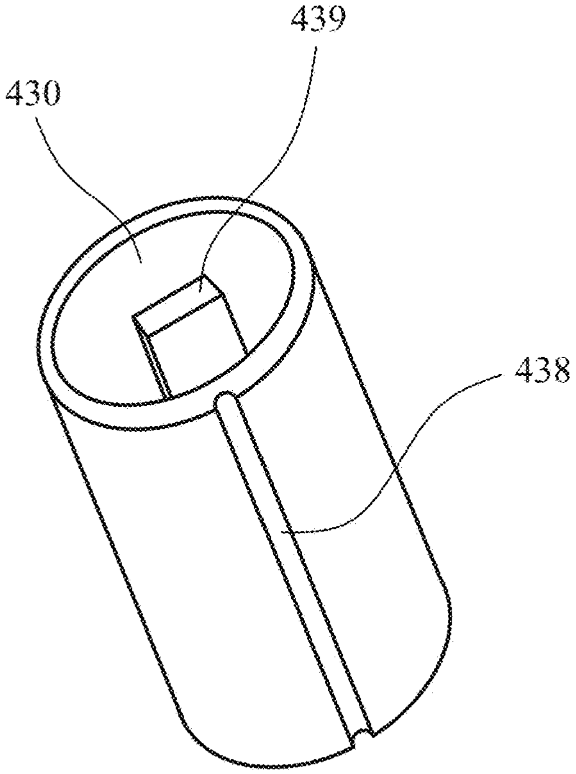
FIG. 6b

AEROSOL-GENERATING SYSTEM INCLUDING A HEATED GEL CONTAINER

CROSS-REFERENCE TO RELATED APPLICATIONS

This application is a continuation of U.S. application Ser. No. 16/997,086, filed on Aug. 19, 2020, which is a continuation of U.S. application Ser. No. 15/662,536, filed Jul. 28, 2017, which is a continuation of and claims priority to PCT/EP2017/066998, filed on Jul. 6, 2017, and further claims priority to EP 16181949.5, filed on Jul. 29, 2016, each of which are hereby incorporated by reference in their entirety.

BACKGROUND

Field

Example embodiments relate to an aerosol-generating system that heats an aerosol-forming substrate to generate an aerosol, including an aerosol-generating system that heats a gel to form an aerosol.

Description of Related Art

Aerosol-generating systems operate by heating a liquid formulation to generate an aerosol. Typically, aerosol-generating systems comprise a device portion and a cartridge. In some systems, the device portion contains a power supply and control electronics, and the cartridge contains a liquid reservoir holding the liquid formulation, a heater for vapourising the liquid formulation, and a wick that transports the liquid from the liquid reservoir to the heater. However, there is a potential for leakage of the liquid from the liquid reservoir both during transport and storage, and when the cartridge is connected to the device portion. The use of a wick to transport the liquid from the reservoir to the heater may also add complexity to the system.

SUMMARY

An aerosol-generating system may include a device body and a cartridge configured to connect to or be received in the device body. The device body may include an electrical power supply and an electrical heater electrically connected to the electrical power supply. The cartridge may include a substrate container defining a blind cavity containing an aerosol-forming substrate in a form of a gel that is a solid at room temperature. The gel may include an aerosol-former. The electrical heater may be configured to heat the substrate container to generate a vapor without contacting the aerosol-forming substrate.

The electrical heater may be configured to heat the aerosol-forming substrate in the blind cavity.

The aerosol-generating system may further include a mouthpiece separate from the cartridge.

At least one wall of the substrate container is in thermal contact with the electrical heater.

The substrate container may include at least one liquid impermeable and vapour impermeable external wall defining the blind cavity.

The aerosol-generating system may be a handheld aerosol-generating system.

The electrical heater may include a resistive heater.

The electrical heater may be configured to surround at least a portion of the substrate container when the cartridge is connected to or received in the device body.

The electrical heater may include one or more electrically resistive tracks on a flexible insulating substrate.

A cartridge for an aerosol-generating system may include a substrate container defining a blind cavity containing an aerosol-forming substrate in a form of a gel that is a solid at room temperature. The gel may include an aerosol-former. The cartridge may be configured to removably connect to or be received in a device body of the aerosol-generating system.

The substrate container may include at least one liquid impermeable and vapour impermeable external wall defining the blind cavity.

The substrate container may include a sealing element that seals the blind cavity.

The gel may have a melting temperature of at least 60 degrees Celsius.

The gel may be a thermoreversible gel.

The gel may include nicotine or a tobacco product.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 5 illustrates the mouthpiece of the system of FIG. 4.

FIGS. 6*a* and 6*b* illustrate the cartridge of the system of FIG. 4.

DETAILED DESCRIPTION

Figure 1A:
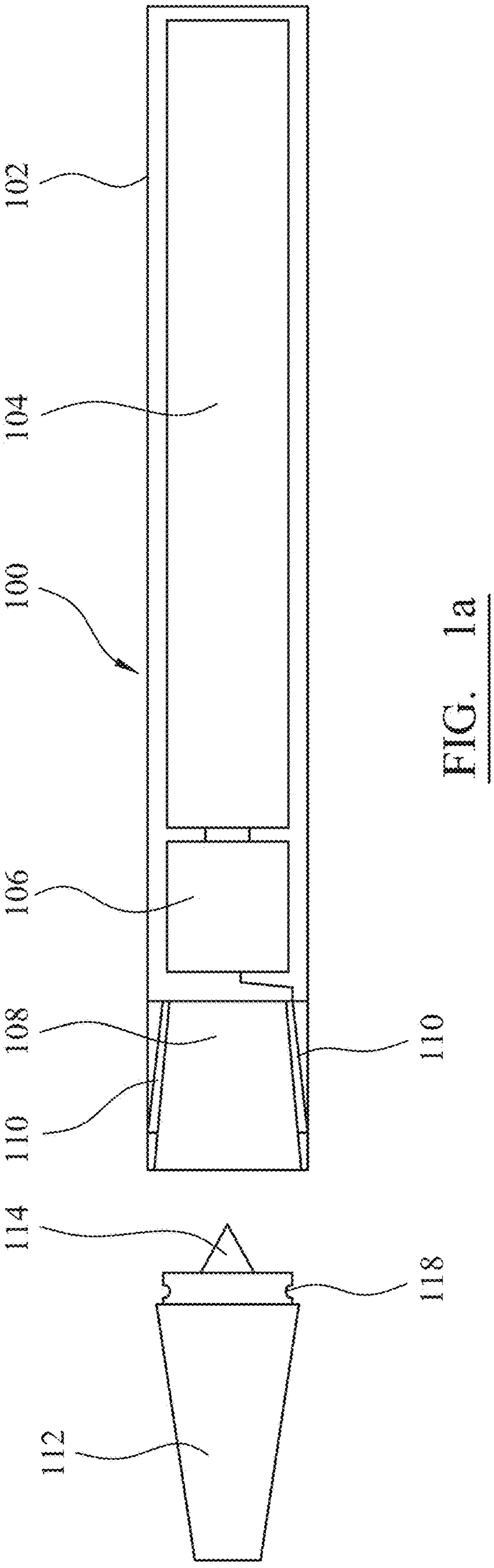
FIG. 1*a* is a schematic illustration of an aerosol-generating device in accordance with an example embodiment.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

In the following description, illustrative embodiments may be described with reference to acts and symbolic representations of operations (e.g., in the form of flow charts, flow diagrams, data flow diagrams, structure diagrams, block diagrams, etc.) that may be implemented as program modules or functional processes including routines, programs, objects, components, data structures, etc., that perform particular tasks or implement particular abstract data types. The operations be implemented using existing hardware in existing electronic systems, such as one or more microprocessors, Central Processing Units (CPUs), digital signal processors (DSPs), application-specific-integrated-circuits (ASICs), SoCs, field programmable gate arrays (FPGAs), computers, or the like.

One or more example embodiments may be (or include) hardware, firmware, hardware executing software, or any combination thereof. Such hardware may include one or more microprocessors, CPUs, SoCs, DSPs, ASICs, FPGAs, computers, or the like, configured as special purpose machines to perform the functions described herein as well as any other well-known functions of these elements. In at least some cases, CPUs, SoCs, DSPs, ASICs and FPGAs may generally be referred to as processing circuits, processors and/or microprocessors.

Although processes may be described with regard to sequential operations, many of the operations may be performed in parallel, concurrently or simultaneously. In addition, the order of the operations may be re-arranged. A process may be terminated when its operations are completed, but may also have additional steps not included in the figure. A process may correspond to a method, function, procedure, subroutine, subprogram, etc. When a process corresponds to a function, its termination may correspond to a return of the function to the calling function or the main function.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit(s), or processing unit(s) may be programmed to perform the necessary tasks, thereby being transformed into special purpose processor(s) or computer(s).

A code segment may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded, or transmitted via any suitable means including memory sharing, message passing, token passing, network transmission, etc.

According to some example embodiments, there is provided an aerosol-generating system comprising: an electrical power supply; an electrical heater connected to the electrical power supply; and a substrate container comprising a blind cavity containing an aerosol-forming substrate in the form of a gel that is solid at room temperature; wherein the electrical heater is external to the substrate container and is configured to heat the substrate container without directly contacting the aerosol-forming substrate to generate a vapour from the aerosol-forming substrate.

In this context, an aerosol-forming substrate is a material or mixture of materials capable of releasing volatile compounds that can form an aerosol. The provision of the aerosol-forming substrate in the form of a gel may be beneficial for storage and transport. By providing the aerosol-forming substrate in a gel, the risk of leakage from the device may be reduced. Replenishing of the device with aerosol forming substrate when depleted or exhausted may also be improved, for example by reducing the risk of leakage or spillage.

"Blind" in this context means closed at one end. In an example embodiment, there is only one aperture for entry to and exit from the cavity.

The heating of the gel without requiring the gel to directly contact the heater reduces the possibility of unwanted materials building up on the heater. If the heater is separate from the gel, the heater can remain clean and so less maintenance may be required and the performance of the system may be more reliable and consistent.

The substrate container may contain other materials in addition to the gel.

The gel may be a solid at room temperature. "Solid" in this context means that the gel has a stable size and shape and does not flow. Room temperature in this context means 25 degrees Celsius.

The gel may comprise an aerosol-former. As used herein, the term "aerosol-former" refers to any suitable known compound or mixture of compounds that, in use, facilitates formation of a dense and stable aerosol. An aerosol-former is substantially resistant to thermal degradation at the operating temperature of the cartridge. Suitable aerosol-formers are well known in the art and include, but are not limited to: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. In an example embodiment, the aerosol formers are polyhydric alcohols or mixtures thereof, such as triethylene glycol, 1,3-butanediol and glycerine or polyethylene glycol.

The gel may comprise a thermoreversible gel. This means that the gel will become fluid when heated to a melting temperature and will set into a gel again at a gelation temperature. The gelation temperature is at or above room temperature and atmospheric pressure. Atmospheric pressure means a pressure of 1 atmosphere. The melting temperature is higher than the gelation temperature. The melting temperature of the gel may be above 50 degrees Celsius (e.g., above 60 degrees Celsius, above 70 degrees Celsius, above 80 degrees Celsius). The melting temperature in this context means the temperature at which the gel is no longer solid and begins to flow. The gel may comprise a gelling agent. The gel may comprise agar or agarose or sodium alginate. The gel may comprise Gellan gum. The gel may comprise a mixture of materials. The gel may comprise water.

The gel may be provided as a single block or may be provided as a plurality of gel elements, for example beads or capsules. The use of beads or capsules may allow for simple refilling of the first (or second) chamber. The use of capsules or beads may also provide a visual as to when a cartridge has already been used, because gel will not form the same capsules or beads on gelation after heating and subsequent cooling.

The gel may comprise nicotine or a tobacco product or another target compound for delivery. When the resulting aerosol is to contain nicotine, the nicotine may be contained in the gel or in another solid form in the substrate container rather than in a liquid. The nicotine can be included in the gel with an aerosol-former. Nicotine is irritating to the skin and can be toxic. Preventing any possible leakage of nicotine by locking the nicotine into a gel at room temperature is therefore desirable.

Flavour compounds may be contained in the second chamber in a gel. Alternatively or in addition, flavour compound may be provided in another form. For example, the second chamber may contain a solid tobacco material that releases flavour compounds when heated. The second chamber may contain, for example, one or more of: powder, granules, pellets, shreds, spaghettis, strips or sheets containing one or more of: herb leaf, tobacco leaf, fragments of tobacco ribs, reconstituted tobacco, homogenised tobacco, extruded tobacco and expanded tobacco. The solid tobacco material in the second chamber may be in loose form. The tobacco may be contained in a gel or liquid. The second chamber may contain additional tobacco or non-tobacco volatile flavour compounds, to be released upon heating.

When agar is used as the gelling agent, the gel may comprise between 0.5 and 5% by weight (e.g., between 0.8 and 1% by weight) agar. The gel may further comprise between 0.1 and 2% by weight nicotine. The gel may further comprise between 30% and 90% by weight (e.g., between 70 and 90% by weight) glycerin. A remainder of the gel may comprise water and any flavourings.

When Gellan gum is used as the gelling agent, the gel may comprise between 0.5 and 5% by weight Gellan gum. The gel may further comprise between 0.1 and 2% by weight nicotine. The gel may further comprise between 30% and 99.4% by weight glycerin. A remainder of the gel may comprise water and any flavourings.

In an example embodiment, the gel comprises 2% by weight nicotine, 70% by weight glycerol, 27% by weight water, and 1% by weight agar. In another example embodiment, the gel comprises 65% by weight glycerol, 20% by weight water, 14.3% by weight tobacco, and by weight agar In an example embodiment, the system does not comprise a transport mechanism for transporting the gel to the electrical heater. The contents of the substrate container may be heated in situ to generate a desired aerosol. In this context, in situ means in the same position within substrate container that the contents are held prior to heating. There is no requirement for a capillary wick or pump. Also, the system does not comprise an additional non-volatile structure within the substrate container for holding or retaining a liquid or gel in proximity to the heater.

The system may comprise a device and a separate consumable portion wherein the consumable portion is configured to connect to or be received in the device, and wherein the device comprises the electrical power supply and the consumable portion comprises the substrate container. The consumable portion may be referred to as a cartridge.

The cartridge can be disposed of and replaced with relative ease when the gel has been depleted. The device may comprise at least a portion of the electrical heater. By providing the heater in the device, the cartridge can be made simpler and relatively inexpensive. The electrical heater may be configured to heat the cartridge to generate a vapour within the cartridge from the gel.

The device may comprise a device housing having a cavity for receiving the cartridge. The cavity of the device may be substantially cylindrical. The cavity may have a diameter substantially equal to or slightly greater than the diameter of the cartridge.

The aerosol-generating device may comprise a device body and may further comprise a mouthpiece separate to the device body. The mouthpiece may be configured for engagement with the device body. The device body may be configured to receive the consumable portion in a cavity of the device body. By providing a reusable mouthpiece, separate to the consumable portion, the construction of the consumable portion can be simple and inexpensive.

At least one wall of the substrate container is in thermal contact with the heater. The at least one wall of the substrate container may be positioned between the heater and the aerosol-forming substrate. The at least one wall of the substrate container may be in direct contact with the heater. The gel within the substrate container can then be heated by conduction through the external wall. The substrate container may comprise at least one liquid impermeable and vapour impermeable external wall defining a blind cavity.

The cartridge may have any suitable shape.

The cartridge may be substantially cylindrical. As used herein, the terms "cylinder" and "cylindrical" refer to a substantially right circular cylinder with a pair of opposed substantially planar end faces.

The cartridge may have any suitable size.

The cartridge may have a length of, for example, between about 5 mm and about 30 mm. In certain embodiments the cartridge may have a length of about 12 mm.

The cartridge may have a diameter of, for example, between about 4 mm and about 10 mm. In certain embodiments the cartridge may have a diameter of about 7 mm.

The substrate container or cartridge may comprise a housing. The housing of the cartridge may be formed from one or more materials. Suitable materials include, but are not limited to, metal, aluminium, polymer, polyether ether ketone (PEEK), polyimides, such as Kapton®, polyethylene terephthalate (PET), polyethylene (PE), polypropylene (PP), polystyrene (PS), fluorinated ethylene propylene (FEP), polytetrafluoroethylene (PTFE), epoxy resins, polyurethane resins and vinyl resins.

The housing of the cartridge may be formed from one or more thermally conductive materials. The interior of the cartridge may be coated or treated to comprise one or more thermally conductive materials. Use of one or more thermally conductive materials to form the cartridge or coat the interior of the cartridge can increase heat transfer from the heater to the gel. Suitable thermally conductive materials include, but are not limited to, metals such as, for example, aluminium, chromium, copper, gold, iron, nickel and silver, alloys, such as brass and steel and ceramics, or combinations thereof. At least one wall of the housing may have a thermal conductivity greater than 10 Watts per metre per Kelvin at room temperature. In an example embodiment, the housing comprises a least one wall formed from aluminium.

In embodiments in which the cartridge is configured to be heated inductively, the housing of the cartridge may comprise a susceptor, for example a susceptor layer. The susceptor layer may for example form a wall of the housing or may be a coating applied to the interior or exterior of the housing. A susceptor may be located within a chamber in the cartridge. For example, the gel may comprise a susceptor material.

Cartridges for use in aerosol-generating systems may be formed by any suitable method. Suitable methods include, but are not limited to, deep drawing, injection moulding, blistering, blow forming and extrusion.

The cartridge may comprise a mouthpiece configured to allow a negative pressure to be applied to the mouthpiece. Where the cartridge comprises a mouthpiece, the mouthpiece may comprise a filter. The filter may have a low particulate filtration efficiency or very low particulate filtration efficiency. Alternatively, the mouthpiece may comprise a hollow tube. The mouthpiece may comprise an airflow modifier, for example a restrictor.

The cartridge may be provided within a mouthpiece tube. The mouthpiece tube may comprise an aerosol-forming chamber. The mouthpiece tube may comprise an airflow restrictor. The mouthpiece tube may comprise a filter. The mouthpiece tube may comprise a cardboard housing. The mouthpiece tube may comprise one or more vapour impermeable elements within the cardboard tube. The mouthpiece tube may have a diameter similar to a cigarette, for example around 7 mm. The mouthpiece tube may have a mouth end through which the aerosol exits. The cartridge may be held in the mouthpiece tube, for example at an opposite end to the mouth end.

An open end of the substrate container may be sealed by one or more frangible barriers.

The one or more frangible barriers may be formed from any suitable material. For example, the one or more frangible barriers may be formed from a foil or film, for example comprising a metal. Where the cartridge comprises one or more frangible barriers sealing one or both of the first chamber and the second chamber, the device body further comprises a piercing member configured to rupture the one or more frangible barriers.

Alternatively, or in addition, the substrate container may be sealed by one or more removable barriers. For example, the substrate container may be sealed by one or more peel-off seals.

The one or more removable barriers may be formed from any suitable material. For example, the one or more removable barriers may be formed from a foil or film, for example comprising a metal.

An open end of the substrate container may be sealed by a vapour permeable element, for example a membrane or mesh configured to allow the escape of vapour from the substrate container through the membrane or mesh. Alternatively, the substrate container may be sealed by a pressure activated valve that allows for the release of vapour through the valve when a pressure difference across the valve exceeds a threshold pressure difference.

The substrate container may comprise a first chamber, containing the gel and a second chamber separate to the first chamber. The second chamber may contain the same gel as the first chamber or may contain a different gel or different material to the first chamber.

The first and second chambers may be fixed together permanently or they may be separable from one another. The first and second chambers may be provided separately and fixed together using a suitable mechanical interlock, such as a snap fitting or a screw fitting. Alternatively, the first and second chambers may remain separate during use.

By providing the first and second chambers separately, a "mix and match" type set of choices may be made available. The contents of the first chamber may provide a particular dosage of a target compound for delivery, such as nicotine, and may provide a particular density of aerosol, and a range of options may be made available. The contents of the second chamber may primarily provide flavour compounds, and a range of options for the second chamber may be available. An adult vaper can choose one chamber from the range of first chambers and one chamber from the range of second chambers and may fit them together to form a complete cartridge.

Even when the first and second chambers are provided together and permanently fixed to one another, the same mix and match approach may be taken by a manufacturer to provide a range of different cartridges.

The first and second chambers may be of the same size and shape as one another or they may have a different size or shape to one another. The size and shape of the first and second chamber may be chosen to suit their contents, and to provide for a particular heating rate in use.

It is also possible to have more than two chambers. It may be desirable to have three or more chambers in the cartridge, with at least two of the chambers having different contents.

The first and second chambers may contain different compositions. Both the first and second chambers may contain a gel. In an example embodiment, neither the first chamber nor the second chamber contains a liquid at room temperature. Also, neither the first chamber nor the second chamber may comprise a liquid retention material or a wicking material.

The first and second chambers may be positioned side by side or one within the other or may be arranged in series such that an air flow can pass first through one chamber and then through the other.

The cartridge may comprise a slot between the first and second chambers. The slot may be configured to receive a heating element. The heating element may be received in the slot for example when the cartridge is installed in an aerosol-forming device. The provision of a slot into which a heating element is received may provide for efficient heating by facilitating that heat energy from the heating element is passed directly to the interior of the substrate container rather than for example heating other elements of the system or the ambient air. The slot may be a blind slot. Blind in this context means closed at one end. The provision of a blind slot allows the heating element to be shielded from the vapour or aerosol generated by the system and can help to prevent the build-up of condensates on the heater.

Where the substrate comprises first and second chambers, the slot may be provided between the first the second chambers. For example, the slot may be provided within a wall separating the first and second chambers.

The electrical heater may comprise a resistive heater. The electrical heater may comprise one or more heating elements.

The electric heating element may comprise one or more external heating elements, one or more internal heating elements, or one or more external heating elements and one or more internal heating elements. In this context, external means outside of the cavity and internal means inside of the cavity of the device.

The one or more external heating elements may comprise an array of external heating elements arranged around the inner surface of the cavity. In certain examples, the external heating elements extend along the longitudinal direction of the cavity. With this arrangement, the heating elements may extend along the same direction in which the cartridge is inserted into and removed from the cavity. This may reduce interference between the heating elements and the cartridge. In some embodiments, the external heating elements extend along the length direction of the cavity and are spaced apart in the circumferential direction. Where the heating element comprises one or more internal heating elements, the one or more internal heating elements may comprise any suitable number of heating elements. For example, the heating element may comprise a single internal heating element. The single internal heating element may extend along the longitudinal direction of the cavity.

The electric heating element may comprise an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, Constantan, nickel-, cobalt-, chromium-, aluminium- titanium- zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation, 1999 Broadway Suite 4300, Denver, Colorado. In composite materials, the electrically resistive material may optionally be embedded in, encapsulated or coated with an insulating material or vice-versa, depending on the kinetics of energy transfer and the external physicochemical properties required. The heating element may comprise a metallic etched foil insulated between two layers of an inert material. In that case, the inert material may comprise Kapton®, all-polyimide or mica foil. Kapton® is a registered trade mark of E.I. du Pont de Nemours and Company, 1007 Market Street, Wilmington, Delaware 19898, United States of America. A flexible heating element of this type may be conformed to the shape of the cavity and may extend around the periphery of the cavity.

The electric heating element may be formed using a metal having a defined relationship between temperature and resistivity. In such embodiments, the metal may be formed as a track between two layers of suitable insulating materials. An electric heating element formed in this manner may be used both as a heater and a temperature sensor.

Where the electric heating element comprises a susceptor, the aerosol-generating device body may comprise an inductor arranged to generate a fluctuating electromagnetic field within the cavity and an electrical power supply connected to the inductor. The inductor may comprise one or more coils that generate a fluctuating electromagnetic field. The coil or coils may surround the cavity.

The device body is capable of generating a fluctuating electromagnetic field of between 1 and 30 MHz, for example, between 2 and 10 MHz, for example between 5 and 7 MHz. The device body is capable of generating a fluctuating electromagnetic field having a field strength (H-field) of between 1 and 5 kA/m, for example between 2 and 3 kA/m, for example about 2.5 kA/m.

The aerosol-generating system may comprise a single heater, which provides for a simpler device construction. The single heater may be configured as an external heater that in use is positioned externally to the cavity. Alternatively, the single heater may be configured as an internal heater that in use is positioned internally to the cavity and received in a slot in the cartridge. In an example embodiment, the single heater is configured as an internal heater.

Where the single heater is configured as an internal heater, the aerosol-generating device may comprise guide means to facilitate proper alignment of the internal heater with the cartridge.

The single heater may be an electric heating element comprising an electrically resistive material. The electric heating element may comprise a non-elastic material, for example a ceramic sintered material, such as glass, alumina ($Al_2O_3$) and silicon nitride ($Si_3N_4$), or printed circuit board or silicon rubber. Alternatively, the electric heating element may comprise an elastic, metallic material, for example an iron alloy or a nickel-chromium alloy.

The single heater may have any shape suitable to heat the cartridge. The electrical heater may be positioned between first and second chambers of the cartridge when the cartridge is connected to or received in the device body. In an example embodiment, the heater does not project from the aerosol-generating device.

The electrical heater may surround the substrate container. The electrical heater may also comprise one or more electrically resistive tracks on a flexible insulating substrate.

The aerosol-generating system may further comprise one or more temperature sensors configured to sense the temperature of at least one of the electrical heating elements. In such embodiments, the system may comprise a controller and the controller may be configured to control a supply of power to the electrical heater based on the sensed temperature. The controller may be configured to supply power to the heater continuously after activation of the system rather than in response to detected puffs. Alternatively, the controller may be configured to supply power to the heater in response to puffs.

The system may comprise electronic circuitry to control the supply of power to the electric heater. The electronic circuitry may be a simple switch. Alternatively the electronic circuitry may comprise one or more microprocessors or microcontrollers. The electronic circuitry may be programmable.

The electrical power supply may be a DC voltage source. In some example embodiments, the power supply is a battery. For example, the power supply may be a Nickel-metal hydride battery, a Nickel cadmium battery, or a Lithium based battery, for example a Lithium-Cobalt, a Lithium-hon-Phosphate or a Lithium-Polymer battery. The power supply may alternatively be another form of charge storage device such as a capacitor. The power supply may require recharging and may have a capacity that allows for the storage of enough energy for use of the aerosol-generating device with one or more aerosol-generating articles.

The aerosol-generating system is configured to generate an aerosol. The aerosol-generating system may be a handheld system and may comprise a mouthpiece on which a negative pressure is applied.

In an example embodiment, the system does not comprise a transport mechanism for transporting the aerosol-former to the heater. The contents of the cartridge may be heated in situ to generate a desired aerosol. In this context, in situ means in the same position within the first and second chambers that the contents are held prior to heating. There is no requirement for a capillary wick or pump.

The aerosol-generating device may be a portable or handheld aerosol-generating device that is comfortable to hold.

The aerosol-generating device may be substantially cylindrical in shape. The aerosol-generating device may have a length of between approximately 70 millimetres and approximately 120 millimetres.

According to some example embodiments, there is provided a cartridge for an aerosol-generating system that includes an electrical heater. The cartridge may comprise a substrate container defining a blind cavity containing an aerosol-forming substrate in the form of a gel that is solid at room temperature, wherein the cartridge is configured to removably connect to or be received in a device body of the aerosol-generating system.

Features of the substrate container and cartridge described in relation to the first aspect of the example embodiments may apply to the substrate container and cartridge of the second aspect of the example embodiments. In particular, the substrate container may comprise at least one liquid and vapour impermeable external wall defining the blind cavity. The blind cavity may be sealed by a frangible, removable, or vapour-permeable sealing element.

Figure 2:
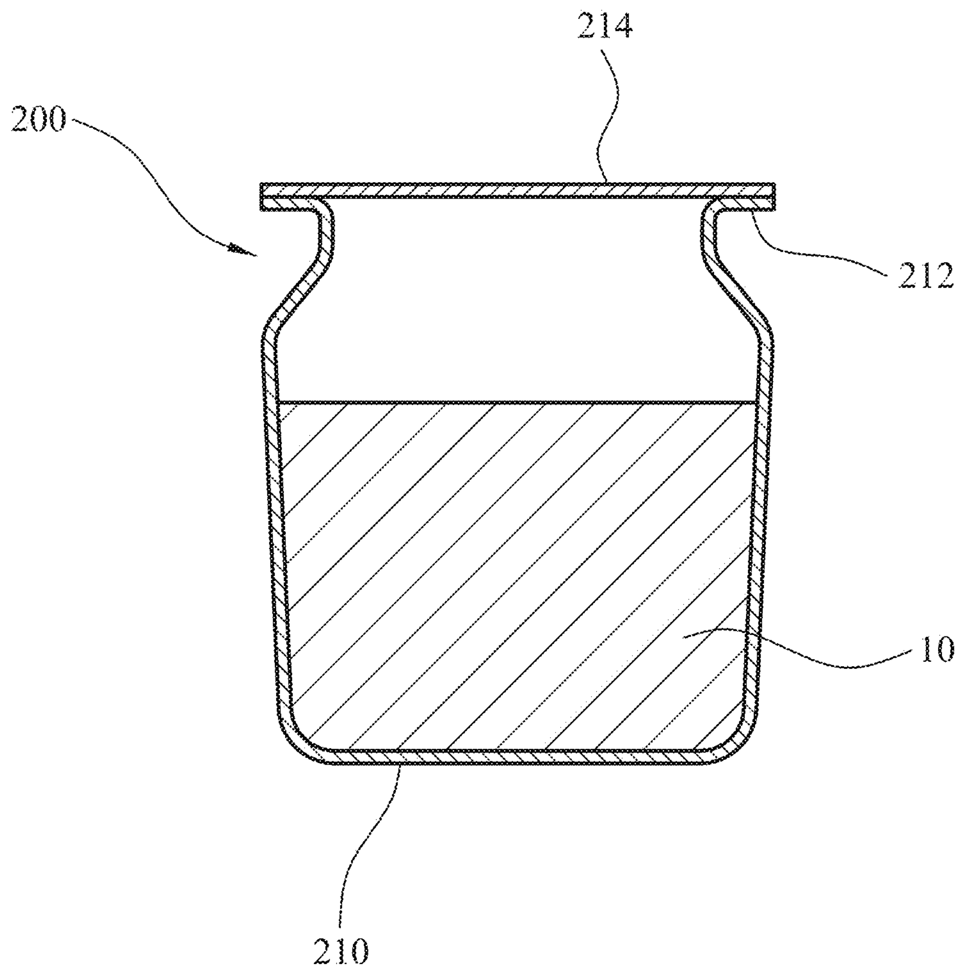
FIG. 2 shows the cartridge of FIG. 1*b* in further detail.

FIG. 1*a* is a schematic illustration of an aerosol-generating device in accordance with an example embodiment. FIG. 1*a* shows a cross-sectional view of an aerosol-generating device 100 for use with a container 200 as shown in FIG. 2. The aerosol-generating device comprises an outer housing 102, containing a power supply 104 such as a rechargeable battery and control electronics or control circuitry 106. The housing 102 further comprises a cavity 108 configured to receive a container 200. A heater 110 extends around the periphery of the cavity 108. The control circuitry is connected to the heater 110. The heater is formed from one or more metal heating tracks sandwiched between two layers of flexible, thermal stable substrate material, such as polyimide. The aerosol-generating device 100 further comprises a mouthpiece 112 attachable to a proximal end of the aerosol-generating device housing 102 by a push fitting or screw fitting. The mouthpiece comprises a piercing portion 114, air inlets 118 and an air outlet 116.

A cartridge or container 200 that is placed in the cavity 108 of the device is shown in FIG. 2. The container has a housing 210 formed from aluminium, which is a good thermal conductor. The housing of the container is in the form of a cup that defines a blind cavity. The housing 210 may be manufactured using suitable known techniques, such as deep drawing. The container contains a gel 10. In this embodiment the gel comprises 2% by weight nicotine, 70% by weight glycerol, 27% by weight water and 1% by weight agar. In another embodiment, the gel comprises 65% by weight glycerol, 20% by weight water, 14.3% by weight solid powdered tobacco and 0.7% by weight agar. The gel is sealed in the cavity of the container by a frangible sealing foil 214. The sealing foil may be welded, heat sealed, or adhered to a lip 212 of the housing 210. This type of container can be made relatively inexpensively.

Figure 1B:
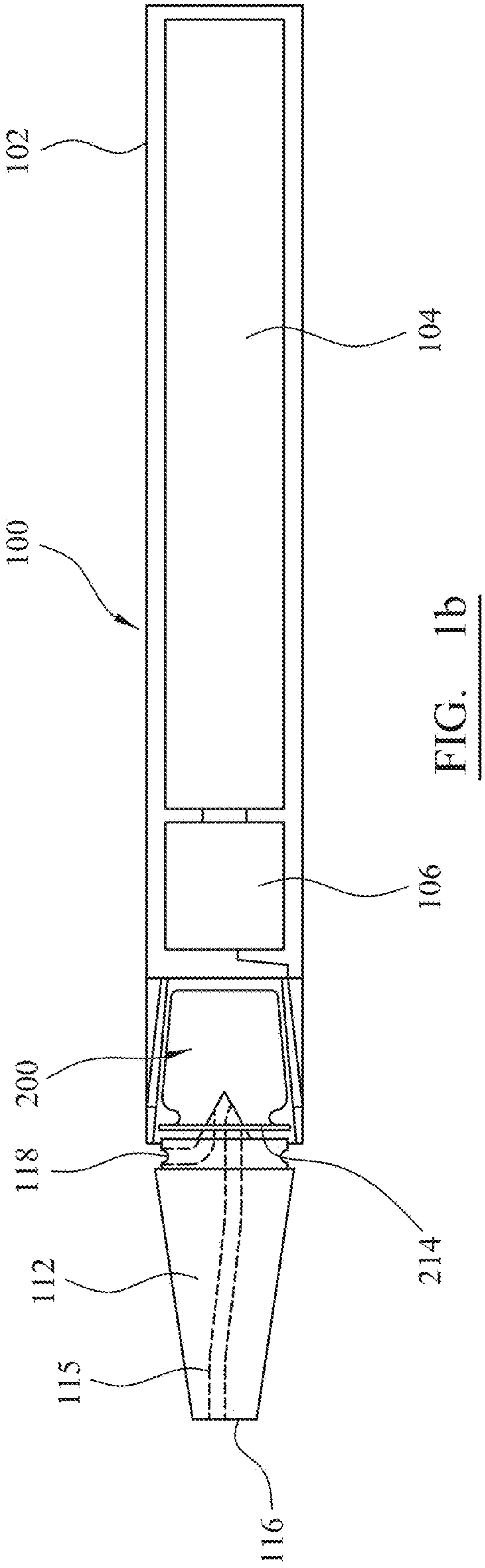
FIG. 1*b* shows the device of FIG. 1*a* with a cartridge received in a cavity of the device.

FIG. 1*b* shows a cross-sectional view of the aerosol-generating device 100 with a container 200 received in the cavity 108 of the housing. In use, the container 200 is inserted into the cavity 108 of the aerosol-generating device 100, and then attaches the mouthpiece 112 to the housing 102. By attaching the mouthpiece, the piercing portion 114 pierces the sealing foil 214 of the container, and forms an airflow pathway 115 from the air inlets 118, through the container to the air outlet. A button (not shown) can be pressed to activate the device. After activating the device, the heater is supplied with power by the control electronics or control circuitry 106 from the power supply 104. The heater then directly heats the external wall of the cartridge. When the temperature of the container 200 reaches the operating temperature of about 250 degrees Celsius, an indicator (not shown) may indicate that a negative pressure may be applied to the mouthpiece at air outlet 116. When a negative pressure is applied to the mouthpiece, air enters the air inlets 118, proceeds through the mouthpiece and into the container 200, entrains vapourised gel, and then exits through the air outlet 116 in the mouthpiece. The heater may operate for a fixed time period after activation (e.g., 6 minutes) or may operate until the system is switched off.

When the gel in the cartridge has become exhausted, the cartridge can be removed and replaced by a new cartridge.

Figure 3:
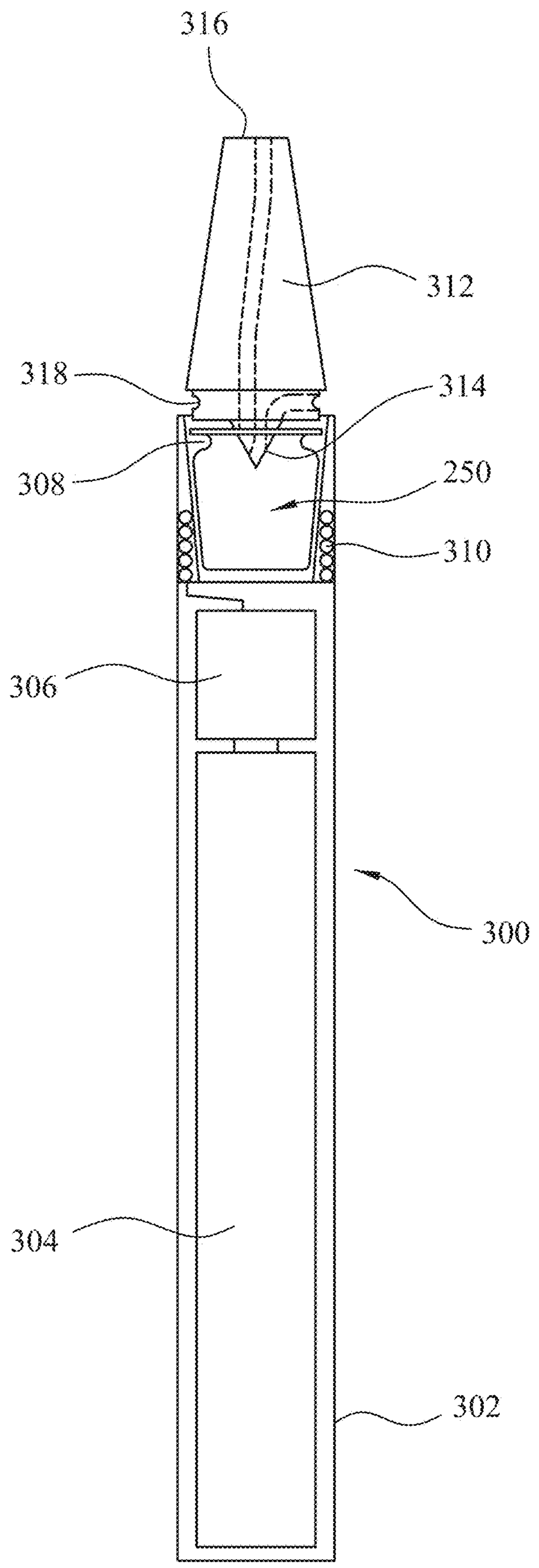
FIG. 3 is a schematic illustration of another aerosol-generating system in accordance with an example embodiment.

FIG. 3 is a schematic illustration of another aerosol-generating system in accordance with an example embodiment. The example embodiment of FIG. 3 is operated by using induction heating rather than by using resistive heating. Instead of using a resistive heater around the cavity in which the cartridge is received, the device comprises an induction coil 310 surrounding the cavity and a susceptor is provided in the cavity in this example as part of the cartridge.

The aerosol-generating device comprises an outer housing 302, containing a power supply 304 such as a rechargeable battery and control circuitry 306. The housing 302 further comprises a cavity 308 configured to receive a cartridge or container 250. An induction coil is positioned around the periphery of the cavity 308. The control circuitry is connected to the induction coil 310. The control circuitry includes components to generate an AC signal which is provided to the induction coil 310. The aerosol-generating device 100 further comprises a mouthpiece 312 attachable to a proximal end of the aerosol-generating device housing 302 by a push fitting or screw fitting. The mouthpiece comprises a piercing portion 314, and air inlets 318 and an air outlet 316 in the same manner as the embodiment of FIG. 1.

The cartridge or container 250 of FIG. 3 is similar to the cartridge shown in FIG. 2. The composition of the gel may be the same as in the embodiment of FIG. 1. However, the housing of the cartridge comprises a susceptor material that heats up in the alternating magnetic field. The susceptor may be provided as a coating on the inside or outside of the housing or may be within housing itself. The susceptor material in this example is stainless steel, which is provided as part of the cartridge rather than part of the device body, but it is possible for the susceptor material to be provided as part of the device body or both in the cartridge and the device body. The entire cartridge may be formed from a susceptor material, or a susceptor material may be provided as a coating or layer on one of more surfaces of the cartridge. It is also possible to provide susceptor material within the first and second chambers, suspended in the gel or other material contained there.

In operation, the system is configured to operate in a continuous heating mode as in the embodiment of FIG. 1. This means that when the device is switched on, the device supplies an AC signal to the induction coil in order to generate an alternating magnetic field in the cavity. This induces current flow in the susceptor resulting in a heating of the susceptor. If a ferromagnetic material is used as the susceptor, hysteresis losses may also contribute to the heating. The induction coil may be described as an induction heater in this context. By controlling the magnitude and frequency of the AC signal, the temperature within the cartridge or container 250 can be controlled. A temperature sensor may be provided within the cavity 308 and a feedback control loop used. The induction heater may operate for a fixed time period after activation (e.g., 6 minutes) or may operate until the system is switched off.

Figure 4:
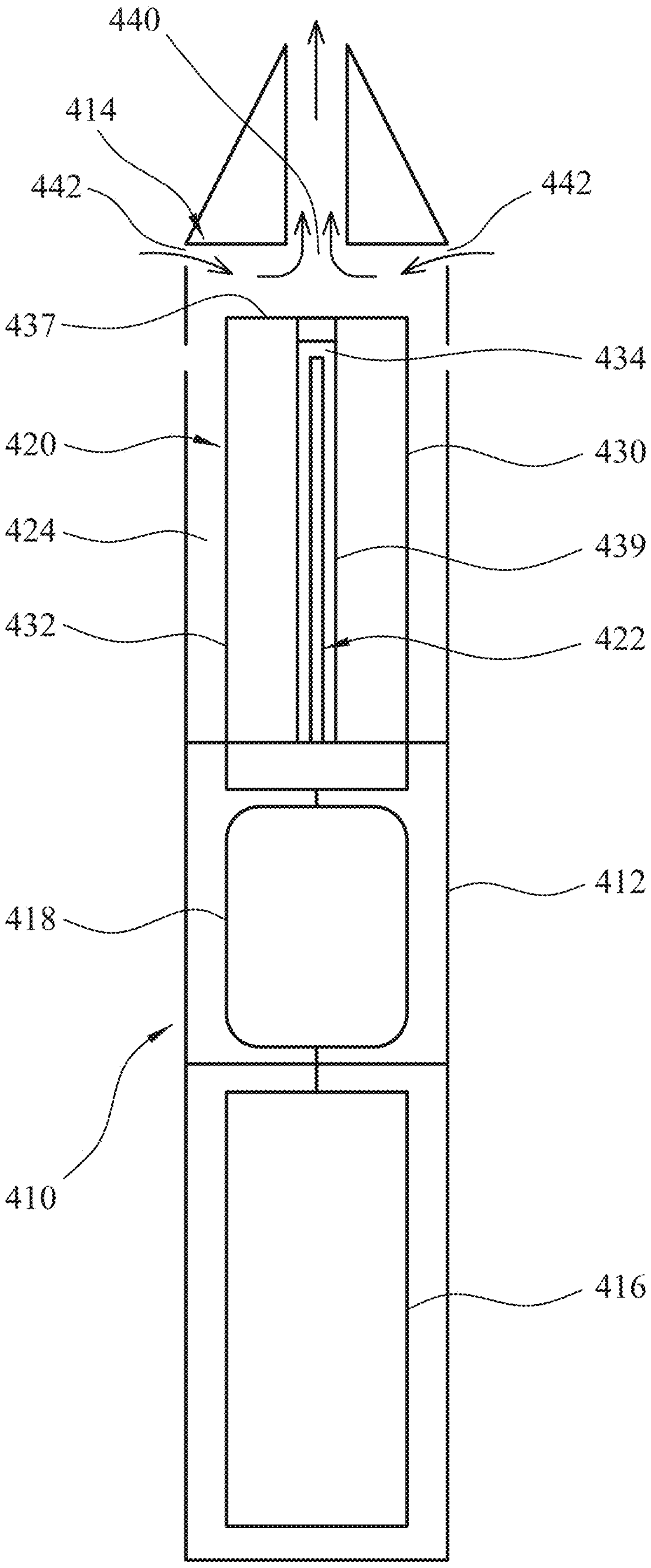
FIG. 4 is a schematic illustration of another aerosol-generating system in accordance with an example embodiment.

FIG. 4 is a schematic illustration of another aerosol-generating system in accordance with an example embodiment. The system comprises an aerosol-generating device 410 and a replaceable cartridge 420. The aerosol-generating device comprises a device body 412 and a mouthpiece portion 414.

The device body 412 comprises a power supply, which is a lithium ion battery 416 and electronic control circuitry 418. The device body also includes heater 422, which is in the form a blade that projects into a cavity 424 in the housing of the device body. The heater is an electric heater comprising an electrically resistive track on a ceramic substrate material. The control circuitry is configured to control the supply of power from the battery 416 to the electric heater 422.

The mouthpiece portion 414 engages the device body using a simple push fitting, although any type of connection, such as a snap fitting or screw fitting may be used. The mouthpiece portion in this embodiment is simply a tapered hollow tube, without any filter elements, and is shown in more detail in FIG. 5. However, it is possible to include one or more filter elements in the mouthpiece portion. The mouthpiece portion comprises air inlet holes 442 and encloses an aerosol-forming chamber 440 (shown in FIG. 4) in which vapour can condense in an airflow prior to exiting the system.

The cartridge 420 comprises a housing defining a blind chamber. The chamber 430 is open at a mouthpiece end. A membrane 437 (shown in FIG. 4) seals the open end of the chamber. A removable seal may be provided over the membrane, wherein the seal is subsequently peeled off. A blind slot 434 is provided that extends into the chamber for the heater 422 to be received in. The blind slot 434 is surrounded by a slot wall 439 and is closed at the mouthpiece end so that the heater does not contact the contents the contents of the chamber. The chamber 430 holds a gel, containing nicotine and aerosol-former, as described with reference to the embodiment of FIG. 2.

FIG. 6*a* is a bottom perspective view of the cartridge housing. FIG. 6*b* is a perspective view of the cartridge housing. The cartridge 420 has a housing having a generally cylindrical shape. The slot wall 439 extends into the chamber. The blind slot 434 is within the slot wall. A channel 438 is provided in a wall of the cartridge housing to engage a corresponding rib in the cavity 424. This ensures that the cartridge can only be inserted into the cavity 424 in one orientation, in which the heater blade is received in the slot 434.

The gel in the first chamber 430 comprises one or two aerosol formers such as glycerine, propylene glycol, and polyethylene glycol. The relative concentration of the aerosol formers can be adapted to the particular requirements of the system. In this embodiment the gel in the first chamber 430 comprises (by weight): 2% nicotine, 70% glycerin, 27% water, 1% agar.

The gelling agent may be agar, which has the property of melting at temperatures above 85° C. and turning back to gel at around 40° C. This property makes it suitable for relatively hot environments. For example, the gel will not melt at 50° C., which is useful if the system is left in a hot automobile in the sun. A phase transition to liquid at around 85° C. means that the gel only needs to be heated to a relatively low-temperature to induce aerosolization, allowing low energy consumption. It may be beneficial to use only agarose, which is one of the components of agar, instead of agar.

Further or different flavors, such as menthol, can be added either in water or in the aerosol former prior to the formation of the gel.

The amount of gel provided in the cartridge can also be chosen to suit particular needs. For instance, the cartridge may contain enough gel to provide a single-occasion quantity for vaping or may contain sufficient gel for a multiple-occasion quantity for vaping.

In operation, the system is configured to operate in a continuous heating mode. This means that the heater 422 heats the cartridge throughout an operating session rather than in response to sensed puffs. The system may be turned on using a relatively simple switch (not shown) such that the heater heats the cartridge. A temperature sensor may be included in the system so that an indication can be provided as to when an operating temperature has been reached, at which aerosol is generated. The gel becomes liquid upon heating above 85° C. Aerosol containing nicotine and glycerin is generated at temperatures between 180° C. to 250° C. During operation, the heater operates at approximately 250° C. The heater may operate for a fixed time period after activation (e.g., 6 minutes) or may operate until the system is switched off. The operating time may depend on the amount of gel contained within the cartridge.

The cartridge housing is formed of aluminium, which is a good thermal conductor. The heater is not in contact with the gel or any generated vapour or aerosol. It is held in the blind slot 434 and so is isolated from the generated aerosol. This ensures that there is no build-up of condensates on the heater, which might lead to the generation of undesirable compounds in operation.

Figure 7A:
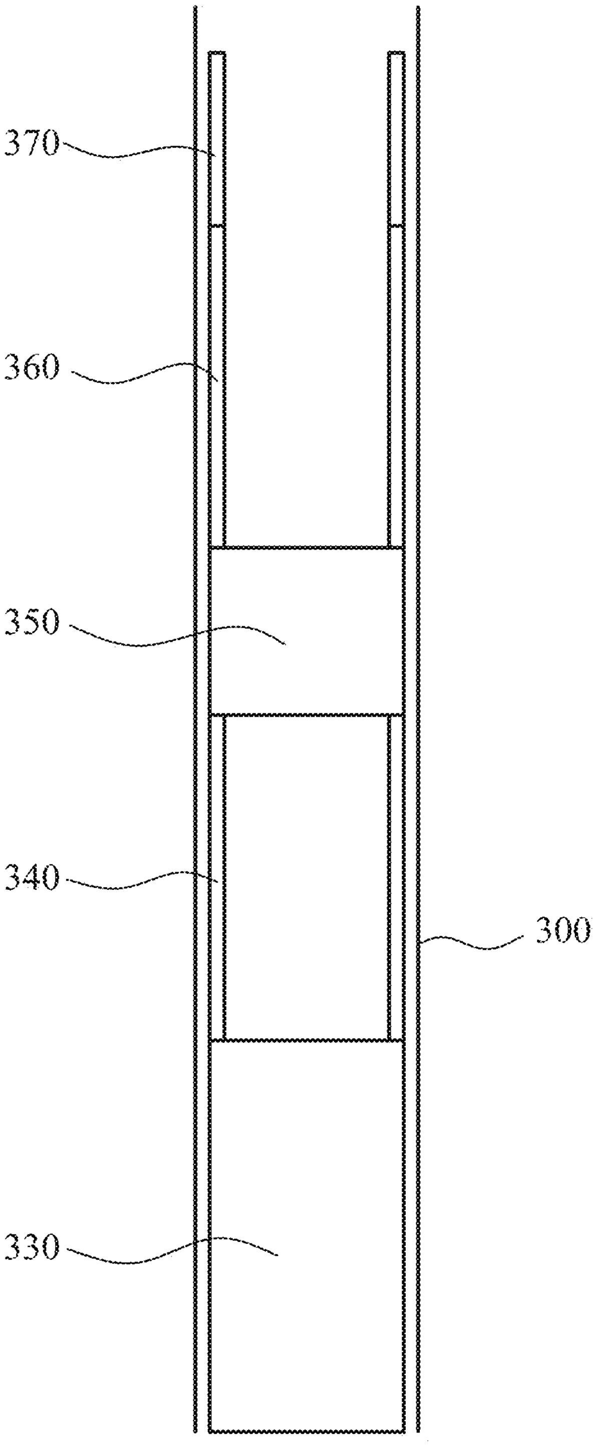
FIGS. 7*a* and 7*b* are schematic illustrations of another cartridge in accordance with an example embodiment.
Figure 7B:
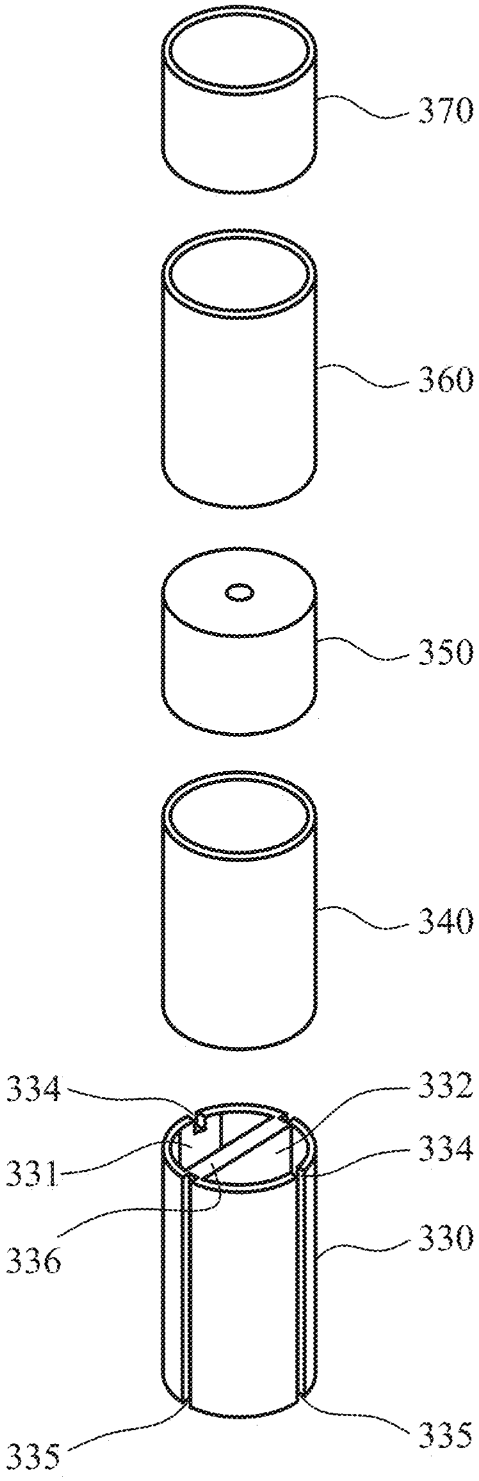

FIGS. 7*a* and 7*b* are schematic illustrations of a cartridge in accordance with an example embodiment. In the embodiment of FIG. 7*a*, the cartridge 330 is held within a mouthpiece tube 300. A flow restrictor 350 and lining tubes 340, 360, 370 are also held within the mouthpiece tube. The components held within the mouthpiece tube 300 are shown in an exploded view in FIG. 7*b*.

The cartridge 330 is similar to the cartridge shown in FIGS. 6*a* and 6*b*. The cartridge 330 has a generally cylindrical shape. However, the cartridge 330 comprises a housing defining two blind chambers. The first and second chambers are of equal size and shape and are separated by a dividing wall 336. The two chambers 331, 332 are open at a mouthpiece end. A blind slot is provided in the dividing wall 336 between the two chambers for the heater to be received in. The blind slot is closed at the mouthpiece end. The first chamber 331 holds a first gel, containing nicotine and aerosol-former, and the second chamber 332 holds a second gel, containing shredded tobacco leaves.

The cartridge 330 has no membrane or sealing element but includes airflow channels 335 formed in the walls of the cartridge and air inlets 334 at the top of the airflow channels to allow air into the open ends of the first and second chambers.

The mouthpiece tube is formed from cardboard and has a diameter of 6.6 mm and a length of 45 mm. Lining tubes 340 are formed from polyetheretherketone (PEEK) and are provided to prevent the cardboard mouthpiece tube from absorbing moisture from within the mouthpiece tube. The lining tubes can be made very thin, in this embodiment having a thickness of 0.3 mm. A restrictor 350 is provided to restrict the airflow to ensure mixing of air with vapour from the cartridge and ensure the generation of an aerosol within the space following the restrictor, in lining tube 360.

Figure 8:
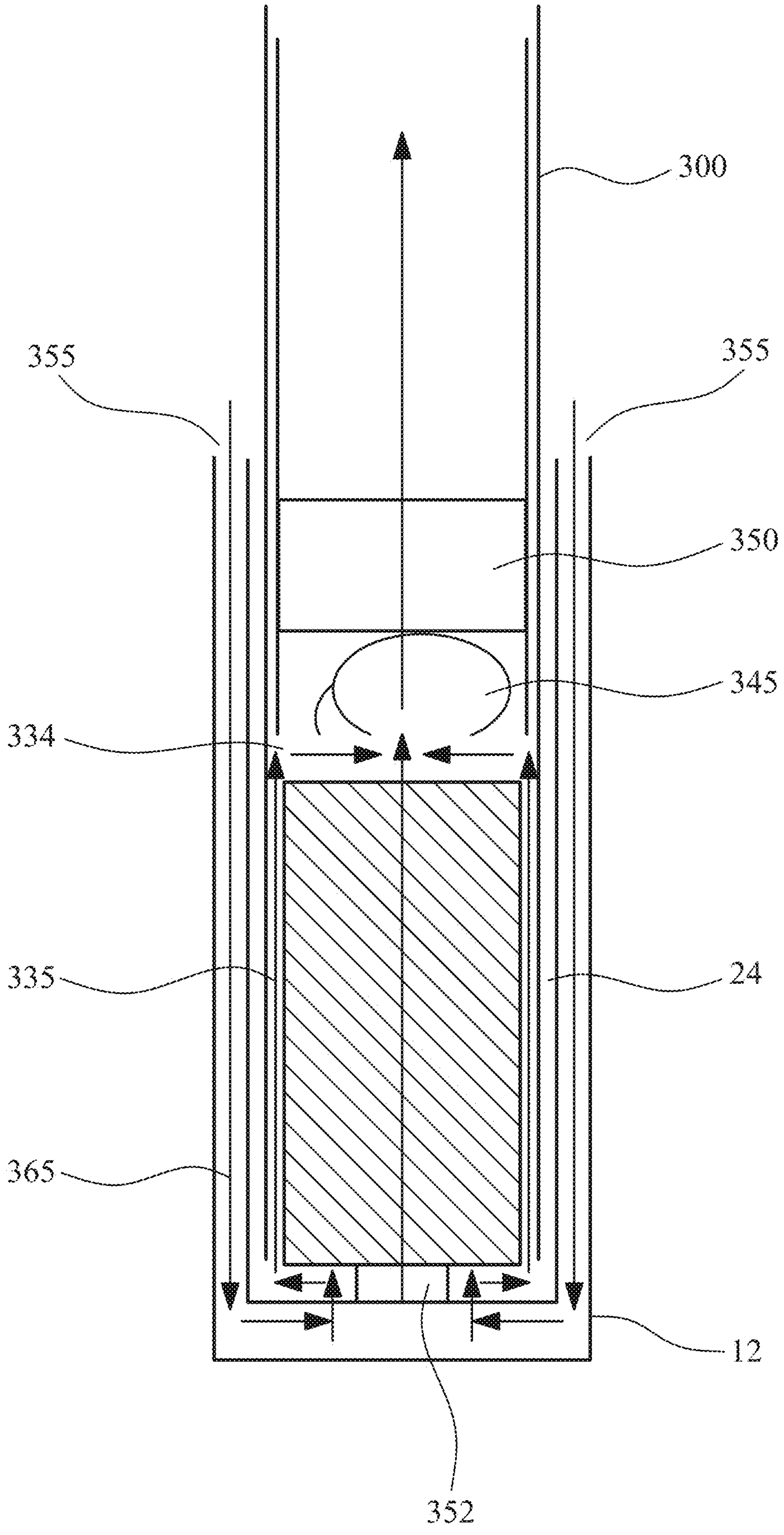
FIG. 8 illustrates the airflow in the system of FIGS. 7*a* and 7*b*.

FIG. 8 illustrates the airflow within the mouthpiece tube of FIG. 7*a* during operation. The mouthpiece tube is shown within the cavity 24 of a device 12 of the type shown in FIG. 1. However, the device of FIG. 8 does not have a mouthpiece. FIG. 8 illustrates only the end of the device that receives the mouthpiece tube. The battery and control circuitry is not shown. The device includes device air inlets 355 that allow air into an internal airflow passage 365 formed in the device around the periphery of the cavity 24. A spacer element 352 is positioned in a base of the cavity to allow air to flow from the internal airflow passage 365 into the cavity 24 and then into the airflow channels 335 in the cartridge 330 and through the air inlets 334 into the interior of the mouthpiece tube.

The cartridge shown in FIGS. 7*a* and 7*b* may be heated by heater of the type shown in FIG. 4 or of the type shown in FIG. 1 or 3. In operation, the system is configured to operate in a continuous heating mode. This means that the heater heats the cartridge throughout an operating session rather than in response to sensed puffs. The system may be turned on using a relatively simple switch (not shown) such that the heater heats the cartridge. The gels in the first and second chambers become liquid upon heating and vapour containing nicotine and glycerin is generated at temperatures between 180° C. to 250° C.

When the system is at the operating temperature, a negative pressure can be applied to a mouth end of the mouthpiece tube to draw air through the mouthpiece tube. Air is drawn into a distal end of the mouthpiece tube, opposite the mouthpiece end from the internal passage 365. The air travels up the airflow channels 335 and through air inlets 334 into space 345. The air mixes in space 345 with vapour from the first and second chambers. The mixed air and vapour then passes through the restrictor 350, after which it cools to continue to form an aerosol before exiting the system. After operation, the mouthpiece tube, including the cartridge, can be withdrawn from the device and disposed of. Mouthpiece tubes of this type may be sold in packs to provide for multiple operations of the system.

The embodiments described have each been described as configured to operate a continuous heating scheme, in which the heater is activated for a desired or predetermined time period. However, the systems described may be configured to operate in different ways. For example, power may be provided to the heater or induction coil for only the duration of each puff, based on signals from an airflow sensor within the system. Alternatively, or in addition, power to the heater or induction coil may be switched on and off in response to an actuation of a button or switch.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims. For instance, different arrangements for airflow through the system may be provided and different heating arrangements can be envisaged, such as non-electrical heaters.

The invention claimed is:

1. A cartridge for an aerosol-generating device, the cartridge comprising:

a peripheral wall defining an airflow channel formed in the peripheral wall and an air inlet in communication with the airflow channel;

a blind chamber at least partially defined by the peripheral wall, the air inlet configured to allow air into the blind chamber; and an aerosol-forming substrate in the blind chamber, the aerosol-forming substrate being in a form of a gel, the gel being solid at room temperature.

2. The cartridge of claim 1, wherein the airflow channel extends along an entire length of the peripheral wall.

3. The cartridge of claim 1, wherein the peripheral wall defines a plurality of airflow channels, the plurality of airflow channels including the airflow channel.

4. The cartridge of claim 1, further comprising:

a dividing wall fixed to the peripheral wall and extending through the blind chamber to separate the blind chamber into a first blind chamber portion and a second blind chamber portion.

5. The cartridge of claim 4, wherein the dividing wall defines a slot configured to receive at least a portion of a heater.

6. The cartridge of claim 5, wherein the slot is a blind slot.

7. The cartridge of claim 6, wherein the cartridge extends between a first end and a second end, the blind chamber is open at the first end, and the blind slot is open at the second end.

8. The cartridge of claim 4, further comprising:

a first aerosol-forming substrate including the aerosol-forming substrate, the first aerosol-forming substrate in the form of a first gel, the first gel including the gel; and a second aerosol-forming substrate in the form of a second gel.

9. The cartridge of claim 8, wherein the first gel is in the form of a first continuous gel mass, and the second gel is in the form of a second continuous gel mass.

10. The cartridge of claim 8, wherein the first gel is in the form of a first plurality of gel beads, and the second gel is in the form of a second plurality of gel beads.

11. The cartridge of claim 1, wherein the peripheral wall includes a thermally conductive material.

12. The cartridge of claim 11, wherein the thermally conductive material includes aluminum, chromium, copper, gold, iron, nickel, silver, brass, steel, a ceramic, or any combination thereof.

13. The cartridge of claim 1, wherein the peripheral wall defines an alignment channel configured to receive a portion of the aerosol-generating device to facilitate alignment of the cartridge within the aerosol-generating device.

14. The cartridge of claim 1, wherein the cartridge is free of a wick.

15. The cartridge of claim 1, further comprising:

a mouthpiece.

16. The cartridge of claim 15, wherein the mouthpiece defines an air inlet hole.

17. The cartridge of claim 15, wherein the mouthpiece includes, a filter.

18. The cartridge of claim 1, further comprising:

one or more frangible barriers sealing the blind chamber.

19. The cartridge of claim 1, wherein the cartridge defines a length ranging from 5 mm to 30 mm, and the cartridge defines a diameter ranging from 4 mm to 10 mm.

20. The cartridge of claim 1, wherein the cartridge is substantially cylindrical.

* * * * *